(12) United States Patent
Chow et al.

(10) Patent No.: US 11,999,956 B2
(45) Date of Patent: Jun. 4, 2024

(54) TARGETED THERAPY COMPOSITION AND ITS USE FOR SUPPRESSING BREAST CANCER CELL PROLIFERATION, MIGRATION OR INVASION

(71) Applicant: NATIONAL CHENG KUNG UNIVERSITY, Tainan (TW)

(72) Inventors: Nan-Haw Chow, Tainan (TW); Yi-Wen Wang, Tainan (TW); Yih-Lin Tuan, Tainan (TW); Yao-Lung Kuo, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 0 days.

(21) Appl. No.: 17/930,136

(22) Filed: Sep. 7, 2022

(65) Prior Publication Data

US 2023/0089224 A1    Mar. 23, 2023

Related U.S. Application Data

(60) Provisional application No. 63/243,215, filed on Sep. 13, 2021.

(51) Int. Cl.
| | |
|---|---|
| *C12N 15/113* | (2010.01) |
| *A61K 31/155* | (2006.01) |
| *A61K 31/713* | (2006.01) |
| *A61P 35/00* | (2006.01) |

(52) U.S. Cl.
CPC ........ *C12N 15/1135* (2013.01); *A61K 31/155* (2013.01); *A61K 31/713* (2013.01); *A61P 35/00* (2018.01); *C12N 2310/14* (2013.01); *C12N 2320/31* (2013.01)

(58) Field of Classification Search
CPC ............ C12N 15/1135; C12N 2310/14; C12N 2320/31; A61K 31/155; A61K 31/713; A61P 35/00
See application file for complete search history.

(56) References Cited

FOREIGN PATENT DOCUMENTS

WO    WO-2021075853 A1 *    4/2021

* cited by examiner

*Primary Examiner* — J. E. Angell
(74) *Attorney, Agent, or Firm* — Locke Lord LLP; Tim Tingkang Xia, Esq.

(57) ABSTRACT

The present invention discloses a targeted therapy composition and a method for suppressing breast cancer cell proliferation, migration or invasion by administrating the targeted therapy composition to a subject in need thereof. The composition comprises a type 3 epithelial membrane proteins (EMP3) targeted inhibitor. The breast cancer cells are characterized by upregulation of EMP3, EGFR, HER2, HER3, HR, or downregulation of HER4 gene expression. EMP3-targeting oligonucleotide or nuclease is administrated upon the breast cancer cells so as to degrade EMP3-coding DNA or mRNA, and to suppress breast cancer cell proliferation, migration or invasion.

11 Claims, 15 Drawing Sheets

Specification includes a Sequence Listing.

```
  1 ggaggcccga gcgagggaca agactccgac tccagctctg acttttttcg cggctctcgg
 61 cttccattgc accaatctca ctcctctgc tgtgtctc agcctcac atcttcatc
121 tatactgct ttcatggcc acttgaaca agttgtgt gacttcctt gggaagag A target region 181 ccctgaatct ctggtacgac tgcacgtgga acaacgacac caaaacatgg gcctgcagta
241 atgtcagcga gaatggctgg ctgaaggcgg tgcaggtcct catggtgctc tccctcatc
301 tctgctgtct ctcctgtgt ctgttcatgt tccagctcta caccatgcga cgaggagtc B target region 361 tcttctatgc caccggcctc tgccagcttt gcaccagcgt ggcggtgttt actggcgcct
421 tgatctatgc cattcacgcc gaggagatcc tggagaagca cccgcgaggg ggcagcttcg
481 gatactgctt cgccctggcc tgggtggcct tccccctcgc cctgtcagc ggcatcatct
541 acatccacct acggaagcgg gagtgagcgc cccgcctcgc tcggctgccc ccgcccttc
601 ccggccccc tcgccgcgcg tcctccaaaa aataaaacct taaccgcgg (SEQ NO:5, EMP3 mRNA)
```

FIG. 1

TARGETED THERAPY COMPOSITION AND ITS USE FOR SUPPRESSING BREAST CANCER CELL PROLIFERATION, MIGRATION OR INVASION

CROSS REFERENCE TO RELATED APPLICATION

This application claims the benefit of provisional application Ser. No. 63/243,215, filed Sep. 13, 2021.

STATEMENT REGARDING SEQUENCE LISTING

Reference to sequence listing is submitted electronically via EFS-web. The content of the electronically submitted sequence listing (Name: PI-110-108-US-SEQUENCE LISTING.xml, Size: 6,208 bytes; and Date of Creation: Dec. 19, 2023) is incorporated herein by reference in its entirety.

FIELD OF THE INVENTION

The present invention is related to a composition, especially a composition for targeted therapy and specific to breast cancer cell proliferation, migration or invasion.

BACKGROUND OF THE INVENTION

Breast cancer (BC) is the most commonly diagnosed cancer worldwide and accounts for 684,996 (6.9%) cancer-related deaths in 2020. Accumulating evidence indicate that BC encompasses heterogeneous subgroups at the molecular, histopathologic and clinical levels. BC consists of 3 major tumor subtypes categorized according to presence or absence of expression for estrogen receptor (ER), progesterone receptor (PR) and/or amplification of human epidermal growth factor 2 (HER2). The hormone receptor (HR) positive/HER2-negative, HER2-positive, and triple-negative tumors (lacking all three standard molecular markers) represent 70%, 15-20%, and 15% of BC patients, respectively.

Both surgery and radiation therapy are considered local treatment. Both surgery and radiation therapy are considered local treatment. Systemic treatments include chemotherapy, hormone therapy, and targeted therapy. Recent advancements further support for multimodal approach to improve patient prognosis, including adjunct immunotherapy.

Current standards of treatment strategy for each BC patient depend on tumor subtype, anatomic cancer staging, and patient preferences. For instance, hormone therapeutic agents are the primary systemic therapy for ER-positive or PR-positive BCs. HER2-targeted therapy using monoclonal antibodies, antibody-drug conjugates or tyrosine kinase inhibitors is designed for HER2-positive BC patients that usually associated with poor prognosis and chemotherapy resistance. Introduction of anti-HER2 therapies has led to dramatic improvements of patients with HER2-positive BC in survival for both early and advanced stages.

However, development of resistance to targeted drugs is almost unavoidable, emphasizing the importance of biochemical and pharmaceutical advances to improve treatment outcome. Moreover, a crosstalk between HER2 and ER pathways may also contribute to endocrine resistance. As a result, discovery of the mechanisms underlying trastuzumab resistance and development of innovative therapies are indispensable in the design of precision medicine for BC patients.

The epithelial membrane proteins (EMPs) belong to growth arrest-specific 3 gene family and plays a vital role in cell migration, growth, and differentiation. The EMP3, 4-transmembrane glycoprotein, one of the EMP family members, has received increased attention in recent years for its potential role in the pathogenesis of human cancer. Level of EMP3 mRNA was significantly higher in breast cancer than that of normal tissue. EMP3 expression was associated with invasive phenotype of mammary carcinoma cell lines.

Previous studies have reported that knocking down of EMP3 in SKBR3 cells inhibited tumor growth in vitro, suggesting that EMP3 may be an oncogene for human breast cancer. In addition, EMP3 is up-regulated in association with epithelial-mesenchymal transition (EMT) and is one of the EMT signature genes in vitro. All of 6 cancer stem cells (CSC)-like cell lines are "Basal B" type and have high EMP3 expression too.

Further support for EMP3 in human BC comes from the observation that EMP3 is one of the significantly up-regulated genes in microarray profiling of HER2 overexpression in immortalized luminal human mammary epithelial cells and showed a dose-dependent relationship with HER2 status in vitro.

SUMMARY OF THE INVENTION

To address the issue, experiments in vitro using forward and reverse transfection were performed on appropriate BC cell lines to test hypothesis of the instant applicant. Then, SCID model was created to examine the effects of targeting on EMP3 in vivo. The potential clinical significance of EMP3 as a novel therapeutic target for human breast cancer is an imperative move. Moreover, a functional crosstalk between HER2 and EMP3 in vitro is also revealed. Overexpression of EMP3 in primary BC seemed to positively relate to HER2 protein expression, high histological grading, and nodal metastasis.

The instant applicant is motivated by potential clinical significance of EMP3 upon human BC to provide a targeted therapy composition for suppressing breast cancer cell proliferation, migration or invasion after multiple attempts, wherein the composition comprises an effective dosage of EMP3-targeting inhibitor.

Preferably, breast cancer cells are characterized by up-regulated epidermal growth factor receptor (EGFR) gene, HER2 gene, human epidermal growth factor receptor 3 (HER3) gene, human epidermal growth factor receptor 4 (HER4) gene, HR gene or a combination of two or more thereof.

Preferably, breast cancer cells are characterized by down-regulated HER4 gene.

Preferably, breast cancer cells are selected from a group consisting of hormone receptor (HR) positive breast cancer cell, human epidermal growth factor receptor 2 (HER2) positive breast cancer cell and triple negative breast cancer cell.

Preferably, the EMP3-targeting inhibitor comprises an oligonucleotide or a nuclease.

Preferably, the EMP3-targeting inhibitor targets specifically to EMP3 mRNA.

Preferably, the oligonucleotide is selected from a group consisting of plasmid DNA fragment, RNA interference (RNAi), antisense nucleic acid, DNA/RAN chimeric oligonucleotide, and the oligonucleotide hybridizes with EMP3 coding DNA or mRNA by complementary base pairing.

Preferably, the oligonucleotide comprises a complementary sequence, wherein the complementary sequence hybridizes to a nucleotide sequence of $61^{st}$ to $180^{th}$ or $241^{st}$ to $360^{th}$ base pairs of the mRNA by complementary base pairing.

Preferably, the RNA interference comprises a small interfering RNA, short hairpin RNA, microRNA or a combination thereof.

Preferably, the complementary sequence comprises SEQ NO: 1 or SEQ NO: 2.

Preferably, the plasmid DNA fragment is carried by a vector comprising a promoter upstream the plasmid DNA fragment so as to amplify productions of the RNA interference or the antisense nucleic acid.

Preferably, the plasmid DNA fragment comprises SEQ NO: 3 or SEQ NO: 4.

On the other hand, in order to realize application of the aforementioned targeted therapy composition to clinical breast cancer patients, the present invention further provides a method for suppressing breast cancer cell proliferation, migration or invasion, comprising administrating the aforementioned targeted therapy composition to a subject in need thereof.

Preferably, the method comprises sequentially or separately administrating the targeted therapy composition and Metformin to the subject in need, wherein the targeted therapy composition is administrated to the subject in need when Metformin is completely excreted, or the targeted therapy composition is administrated to the subject in need at 24 hours post Metformin administration.

Preferably, the subject in need has diabetes.

Preferably, the targeted therapy composition can be administrated in combination with an antidiabetic drug to the subject in need, wherein the subject in need has diabetes.

Preferably, the antidiabetic drug is one or more chosen from a group consisting of alpha-glucosidase inhibitors, thiazolidinediones, sulphonylurea and meglitinides.

Preferably, the targeted therapy composition is further administrated sequentially, simultaneously or separately with insulin to the subject in need, wherein the insulin is a fast-acting insulin, a short-acting insulin, an intermediate-acting insulin, a long-acting insulin or a combination of two or more thereof.

Preferably, the subject in need is human (*Homo sapiens*).

Preferably, the targeted therapy composition is administrated for regulating EMT marker genes or stemness marker genes of the breast cancer cells.

Preferably, the EMT marker genes comprise SOX2 gene, Nanog gene, EpCAM gene, Oct4 gene or a combination of two or more thereof.

Preferably, the stemness marker genes comprise fibronectin gene, twist1/2 gene, vimentin gene, E-cadherin gene or a combination of two or more thereof.

Preferably, the targeted therapy composition is administrated for blocking a FAK/c-Src signaling pathway in breast cancer cells.

Preferably, the FAK/c-Src signaling pathway is selected from a group consisting of FAK-Src-RhoA, Src-JAK2-STAT2, Src-Ras/Raf-1 and ERK1/2 signaling pathway.

BRIEF DESCRIPTION OF THE DRAWINGS

FIG. 1 illustrates target regions of the targeted therapy composition on coding DNA or messenger RNA of EMP3, and represented herein is the messenger RNA of EMP3 comprising SEQ NO:5.

DETAILED DESCRIPTION OF THE INVENTION

Figure 2A:
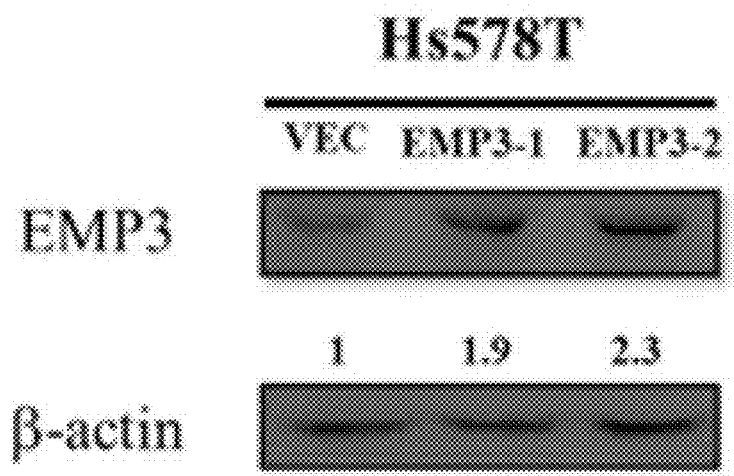
FIG. 2A is a western blot for evaluation of exogenous EMP3 protein overexpression in Hs578T cells.

In one aspect, the present invention aims to provide a targeted therapy composition for suppressing breast cancer cell proliferation, migration or invasion after multiple attempts, wherein the composition comprises an effective dosage of EMP3-targeting inhibitor, wherein the EMP3-targeting inhibitor comprises, but not limited to, an oligonucleotide or a nuclease.

In various embodiments, the oligonucleotide is selected from a group consisting of plasmid DNA fragment, RNA interference (RNAi), antisense nucleic acid, DNA/RNA chimeric oligonucleotide. In particular, the oligonucleotide has a complementary sequence to hybridize with EMP3-coding DNA or mRNA by complementary base pairing so as to achieve EMP3 gene silencing. For instance, RNA interference (RNAi) induces gene silencing through double-stranded RNA. When cells are introduced with a double-stranded RNA homologous to the coding region of endogenous mRNA, a complementary sequence of the double-stranded RNA hybridizes with the homologous mRNA so that mRNA is degraded, silencing gene expression.

In one or various embodiments, the RNA interference comprises small interfering RNA (siRNA), short hairpin RNA (shRNA), microRNA (miRNA) or a combination thereof, wherein these RANi molecules specifically target to EMP3-coding DNA or mRNA. For example, siRNA is produced by cleavage of a precursor double-stranded RNA. Normally, siRNA is a small RNA molecule with a length of 23 to 35 nucleotides, and hybridizes complementarily with mRNA so as to induce mRNA degradation. In addition to siRNA, miRNA is able to induce RNA interference, and miRNA is mostly a nucleic acid with a length of 20 to 22 nucleotides. Moreover, as a precursor of siRNA, shRNA demonstrates similar effects on EMP3 gene silence, and shRNA is characterized by a stem-loop structure which is much similar to a hairpin.

In some embodiments, the oligonucleotide hybridizes with mRNA through a complementary sequence by complementary base pairing, and the mRNA encodes EMP3. In one preferred embodiment, taking human as an example, the mRNA has a reference sequence from NCBI GenBank, with an ID number NM_001425.3. Shown in FIG. 1 are target regions of the oligonucleotide, and the target regions are designated as A and B target regions, respectively. Specifically, the A target region ranges from $61^{st}$ to $180^{th}$ base pairs of the mRNA, while the B target region ranges from $241^{st}$ to $360^{th}$ base pairs of the mRNA. In one preferred embodiment, the complementary sequence comprises SEQ NO: 1 or SEQ NO: 2, targeting to the A target region or the B target region, respectively.

In various embodiments, in addition to naked nucleic molecules such as RNAi or antisense nucleic acid for administration, an expression vector carrying a coding sequence for the naked nucleic acid molecules can be delivered to translation systems of the subject in need by well-known technologies such as transformation, transfection, transduction or gene knock-in. The subject in need can therefore produce the RNAi or the antisense nucleic acid by itself so as to inhibit EMP3 protein expression. Specifically, the vector can be a viral vector, a naked DNA or RNA expression vector, a plasmid, a ligated plasmid, a phage, a DNA or RNA expression vector coated by cation-coagulants, or a DNA or RNA expression vector encapsulated in liposomes, but not limited by this. In some embodiments, the plasmid DNA fragment is carried by an expression vector comprising a promoter upstream the plasmid DNA fragment so as to amplify the RNAi or the antisense nucleic acid. By "promoter", it means a nucleic acid sequence operating gene transcription of a single gene or a gene cluster. Furthermore, the promoter orchestrates an inducible promoter and an enhancer to operate gene transcription of the downstream plasmid DNA fragment. In preferred embodiments, the plasmid DNA fragment comprises SEQ NO: 3 or SEQ NO: 4.

Preferably, in one or various embodiments, the targeted therapy composition specifically targets to breast cancer cells characterized by up-regulated epidermal growth factor receptor (EGFR) gene, HER2 gene, human epidermal growth factor receptor 3 (HER3) gene, human epidermal growth factor receptor 4 (HER4) gene, or HR gene. On the other hand, the breast cancer cells are characterized by down-regulated HER4 gene. In particular, the breast cancer cells are selected from a group consisting of hormone receptor (HR) positive breast cancer cell, human epidermal growth factor receptor 2 (HER2) positive breast cancer cell and triple negative breast cancer cell. By "triple negative breast cancer cell", it means that breast cancer cells are negative for HER2 and HR, including estrogen receptors and progesterone receptors. The present invention is not limited by this, and latest studies have proposed further subtyping of triple negative breast cancer cells in addition to the aforementioned classification.

In another aspect, in order to practically apply the targeted therapy composition to clinical breast cancer patients, present invention further provides a method for suppressing breast cancer cell proliferation, migration or invasion, comprising administrating the aforementioned targeted therapy composition to a subject in need thereof.

In various embodiments, the method comprises sequentially or separately administrating the targeted therapy composition and Metformin to the subject in need, wherein the targeted therapy composition is administrated to the subject in need when Metformin is completely excreted, or the targeted therapy composition is administrated to the subject in need at 24 hours post Metformin administration. Simultaneous administration of Metformin and the targeted therapy composition for breast cancer cells demonstrates less sensitivity to the targeted therapy composition in presence of Metformin.

It is well-known in prior arts that Metformin and its salt promote uptake and metabolism of glucose in muscle cells, and reduce hepatic glycogenesis. Metformin and its salts have been validated to be anti-hyperglycemic, and serve as first-line medicine for treating type 2 diabetes (non-insulin dependent). There is an unusually high proportion of type 2 diabetes patients having colorectal cancer, breast cancer, or pancreatic cancer. Current studies have shown that Metformin and its salts are significantly effective on controlling carcinogenetic risks of type 2 diabetes patients. However, the instant applicant has validated that the targeted therapy composition in the present invention needs to be administrated sequentially or separately with the Metformin to the subject in need to avoid off-target effect led by interferences in between.

Considering the aforementioned off-target effect, breast cancer patients having diabetes need to receive the targeted therapy composition and Metformin in a sequential or a separated manner, or avoids Metformin by using other antidiabetic drugs or insulin, wherein the antidiabetic drug is one or more chosen from a group consisting of alpha-glucosidase inhibitors, thiazolidinediones, sulphonylurea and meglitinides. Exemplarily, the alpha-glucosidase inhibitors can be acarbose or miglitol; the thiazolidinediones can be pioglitazone or rosiglitazone; the sulphonylurea can be glimepiride, glyburide, chlorpropamide or glipizide; and the meglitinides can be repaglinide or nateglinide. The insulin is a fast-acting insulin, a short-acting insulin, an intermediate-acting insulin or a long-acting insulin. The fast-acting insulin can be insulin glulisine, insulin lispro or insulin aspart; the short-acting insulin can be regular insulin; the intermediate-acting insulin can be NPH type human insulin suspension; and the long-acting insulin can be insulin glargine or insulin detemir, but not limited by this.

In various embodiments, the subject in need is a mammal, wherein the mammal can be human, rat, murine, canine, cat, rabbit, goat, bovine or horse. Preferably, the breast cancer cells characterized by up-regulated epidermal growth factor receptor (EGFR) gene, HER2 gene, human epidermal growth factor receptor 3 (HER3) gene, human epidermal growth factor receptor 4 (HER4) gene, or HR gene. More preferably, the breast cancer cells are selected from a group consisting of hormone receptor (HR) positive breast cancer cell, human epidermal growth factor receptor 2 (HER2) positive breast cancer cell and triple negative breast cancer cell.

In some embodiments, the targeted therapy composition is administrated for regulating EMT marker genes or stemness marker genes of breast cancer cells. By "EMT marker genes", it means EMT markers expressed in carcinogenic cells, such as E-cadherin, N-cadherin or vimentin. It is well acknowledged in the field of present invention, activation of EMT is a milestone of carcinogenic cells' transition into metastasis. During EMT, epithelial cells obtain characteristics of mesenchymal cells, and demonstrate higher capability of cell migration and invasion. Specifically, EMT is characterized by knock-down or loss of epithelial marker genes, such as cytokeratin or E-cadherin, while mesenchymal cell markers, such as N-cadherin, vimentin or fibronectin, are up-regulated concurrently. Changes in expression of these cell markers reduce cell adhesion of these cells to neighboring cells. Moreover, secretion of extracellular matrix catabolic enzyme is also increased, which leads to losing features of basal cells. The cells not only reorganize cytoskeletons but also demonstrate enhanced invasive abilities.

By "stem cell markers", it means that stem cell markers expressed in carcinogenic cells, which implicates that carcinogenic cells are transforming into normal stem cells, and show identical biological functions as the normal stem cells, such as cell proliferation. On the other hand, precursor cells may regain capability of self-renewal and cell differentiation, and become carcinogenic cells. For instance, mature somatic cells regain stemness and develop into carcinoma stem cells. The stem cell markers include SOX2 gene, Nanog gene, EpCAM gene, or Oct4 gene, or breast cancer stem cell marker genes, such as aldehyde dehydrogenase 1 (A1/ALDH1A1), BMI-1, CD24, CD44, CD133, Connexin 43/GJA1, CXCR4, DLL4, EpCAM/TROP1, ErbB2/HER2, GLI-1, GLI-2, IL-1 alpha/IL-1F1, CXCR1/IL-8RA, IL-6R alpha, Integrin alpha 6/CD49f, PON1 or PTEN.

Preferably, the targeted therapy composition is administrated for blocking a FAK/c-Src signaling pathway in breast cancer cells. It has been acknowledged in the field of endeavor, increased expression or activity of FAK/c-Src in tumors makes cells more invasive. FAK/c-Src signaling pathway is activated by a variety of receptors, such as platelet-derived growth factor receptor (PDGF-R), epidermal growth factor receptor (EGF-R), fibroblast growth factor receptor (FGF-R), insulin growth factor receptor type 1 (IGF-1R), hepatocyte growth factor (HGF-R), colony stimulating factor 1 receptor (CSF-1R) or stem cell factor receptor (SCF-R). Therefore, FAK/c-Src complex participates in various stages of tumorigenesis, and influences tumor progression, including growth, migration or metastasis. In progression of a breast cancer tumor, FAK/c-Src signaling pathway that is involved includes FAK-Src-RhoA, Src-JAK2-STAT2, Src-Ras/Raf-1 or ERK1/2 signaling pathway.

To further illustrate implementation of present invention, several experimental examples are demonstrated below with specified experimental conditions so as to elaborate technical effects achieved by the present invention. However, contents of the present invention are only exemplified and described herein but not to limit the present invention to any specific aspects.

Cell Culture and Cell Lines

Triple-negative breast cancer (TNBC) cell lines (MDA-MB-231 and Hs578T) were chosen for EMP3 transfection experiments. MDA-MB-231 cells were provided by Professor P. S. Chen (Department of Medical Laboratory Science and Biotechnology, National Cheng Kung University, Taiwan). SKBR3 cells were obtained from the Institute of Clinical Medicine, National Cheng Kung University, Taiwan in 2019. MDA-MB-231 cells lines were maintained in Leibovitz's L-15 medium (Invitrogen [Thermo Fisher Scientific], Carlsbad, CA) supplemented with 10% FBS (Hyclone, Logan, UT) and 1% penicillin/streptomycin (Cassion Laboratories) in a humidified atmosphere containing 5% $CO_2$ at 37° C. Hs578T cells were cultured in Dulbecco's Modified Eagle Medium-High glucose (Hyclone, Logan, UT), supplemented with 0.01 mg/ml insulin, 10% FBS and 1% penicillin/streptomycin in a humidified atmosphere containing 5% $CO_2$ at 37° C.

DNA Constructs and Retrovirus Preparation

The full-length EMP3 cDNA was cloned into pMSCV vector (provided by Professor C. W. Chiang, Institute of Molecular Medicine, National Cheng Kung University, Taiwan). The retroviral expression vectors, pMSCV, harboring EMP3 cDNA, were transfected into GP2-293 cells by the calcium phosphate method, and viral supernatants were prepared by collecting the GP2-293 culture media 48 hours after transfection and centrifugation at 1,500 rpm for 5 minutes. The stable clones were selected by puromycin (5 mg/mL).

Suppression Constructs of EMP3 by miRNA

The constructs of pcDNA6.2-GW/EmGFP-miR-EMP3 were generated using BLOCK-iT Pol II miR RNAi Expression Vector Kits (Invitrogen). Linearized vector pcDNA6.2-GW/EmGFP-miR was ligated to the nucleotide sequence of base pairs 283 to 532, which targets EMP3 CDS. In the following experimental examples, Genbank ID of the EMP3 CDS reference sequence is NM_001425.3, and the chosen EMP3-targeting miRNA sequences are designated as KDK-EMP3-1 and KDK-EMP3-2, respectively. Sequences are listed down in TABLE 1, and negative control was designated as Scramble which does not target any known vertebrate gene.

TABLE 1

| mrRNA | Strands | Sequences |
| --- | --- | --- |
| KDK-EMP3-1 | Top | 5'-tgc tga taa gaa tga gga tgt gaa ggg ttt tgg cca ctg act gac cct tca cac tca ttc tta t-3' |
| | Bottom | 5'-cct gat aag aat gag tgt gaa ggg tca gtc agt ggc caa aac cct tca cat cct cat tct tat c-3' |
| KDK-EMP3-2 | Top | 5'-tgc tga agg aga gac agc aga gaa tgg ttt tgg cca ctg act gac cat tct ctt gtc tct cct t-3' |
| | bottom | 5'-cct gaa gga gag aca aga gaa tgg tca gtc agt ggc caa aac cat tct ctg ctg tct ctc ctt c-3' |
| Scramble- | | 5'-gaa atg tac tgc gcg tgg aga cgt ttt ggc cac tga ctg acg tct cca cgc agt aca ttt-3' |

Western Blotting

Cells were lyzed in a radioimmunoprecipitation assay (RIPA) lysis buffer (Thermo Fisher Scientific Inc., Waltham, MA) and protease inhibitors (Thermo Fisher Scientific Inc., Waltham, MA) were used for protein extraction. Briefly, a total of 30 μg of protein was prepared on a 6 to 12% SDS-PAGE and transferred to a 0.2 to 0.45 μm polyvinylidene difluoride membrane (Stratagene, La Jolla, CA) and blocked by 5% milk (non-fat milk) in Tris Buffered Saline Buffer with Tween 20 (TBST). The membrane was hybridized with primary antibody at 4° C. overnight. The following day, after being washed with TBST for three times, membranes were incubated with secondary antibodies (anti-rabbit or anti-mouse IgG antibody) for 1 hour at room temperature. Detection of protein bands was performed using enhanced chemiluminescence system (Amersham ECL Plus; GE Healthcare, Piscataway, NJ).

Primary antibodies included antibody raised against EMP3, β-actin, EGFR, HER2, HER3, HER4, progesterone receptor, estrogen receptor (GeneTex, Irvine, CA), wherein the dilution rates were all 1:1000 except that β-actin was diluted at 1:5000. The β-actin (ACTB) was used as an internal control.

MTT Assays

To explore the function of EMP3 on breast cancer, MTT assays were performed to evaluate EMP3's effect on cell viability. A total of 1,000 cells after transfection was seeded in 100 μl of medium in each well of 96-well plate and cultured for 24, 48, 72 and 96 hours, respectively. Then, cells were incubated with 50 μl of MTT reagent/well in the dark at 37° C. for 4 hours and amounts of formazan dissolved in dimethyl sulfoxide (DMSO) were quantified by measuring the absorbance of light at 590 nm using an enzyme-labeled meter (SpectraMax i3X, Molecular Devices, LLC, San Jose, CA) so as to establish an index for assessing breast cancer cell survival rate. Four independent experiments were performed in all assays.

Cell Migration and Invasion Assays

Migration and invasion experiments were performed using Boyden chambers consisting of Transwell membrane filter inserts (Cat #3422, Corning Costar, Pittsburgh, PA). In brief, $2.5 \times 10^4$ cells were seeded into each well of a 24-well Transwell chamber (8 μm pore size) for migration assay, or chambers coated with Matrigel for invasion assay, and cultured in complete medium with 10% FBS. Migration and invasion assays were cultured for 48 hr and 72 hr, respectively. Cells on the lower surface of the filter were stained with 2% crystal violet, and those did not penetrate the filter were wiped off. The numbers of migrating or invading cells were counted under a light microscope from five fields in a single chamber (means±SE).

Reverse Transcription-Polymerase Chain Reaction (RT-PCR) and Real-Time PCR Analysis Expression of integrins was examined using RT-PCR. Briefly, RNA (2 μg) was used for reverse transcription to synthesize first-strand cDNA using oligo dT and Moloney murine leukemia virus reverse transcriptase (Promega Technology Enterprise Co., Ltd., Taipei, Taiwan) and stock in −20° C. The cDNA was synthesized from total RNA using a cDNA synthesis kit (Promega) and amplified with SYBR® Green Master Mix (Applied Biosystems, Foster City, CA). β-actin was the internal control.

Wound-Healing Assay

The assay was performed to analyze cell migration in vitro. The culture-inserts (IBIDI GMBH, Munich, Germany) consisting of two wells separated by a 500 μm thick wall were used. The insert was placed into one well of the 6 cm well plate and slightly pressed on the top to ensure tight adhesion. Stable EMP3 overexpress Hs578T, MDA-MB231 cells ($2 \times 10^5$ cells per 100 μl) were seeded into each well and incubated overnight. Then, inserts were removed and the width between gap was recorded at 0, 5, 10 and 15 hours, respectively, by a microscope (Nikon TE300, Tokyo, Japan). The area covered by cells was measured for cell migration in vitro. The encroachment of cell-free dap for each treatment was determined by comparing results to 0 hr time point.

In Vivo Xenograft Model

Six-week-old male NOD/SCID mice were purchased from the NCKU Laboratory Animal Center and maintained in a pathogen-free facility under isothermal conditions with regular photoperiods. The experimental protocol adhered to the regulations of the Animal Protection Act of Taiwan and was approved by the NCKU Laboratory Animal Care and User Committee (108196).

The mice were subcutaneously injected with $1 \times 10^7$ TNBC cells in 200 μl of normal saline on both sides of back. A total of 4 mice with 8 tumors were obtained in each experimental group. Both body weight and tumor size were measured every week. The tumor size was measured directly with ruler. Tumors were resected, photographed, and weighed on day 90.

Statistical Analysis

All data are presented as mean±standard deviation (SD). The data were compared using analysis of variance (ANOVA). Student's t test or Mann-Whitney test. was chosen, as appropriate. Overall survival rate analyzed using Log Rank tests.

Example 1: Biologic Effects of EMP3 on Human Breast Cancer In Vitro

Figure 2B:
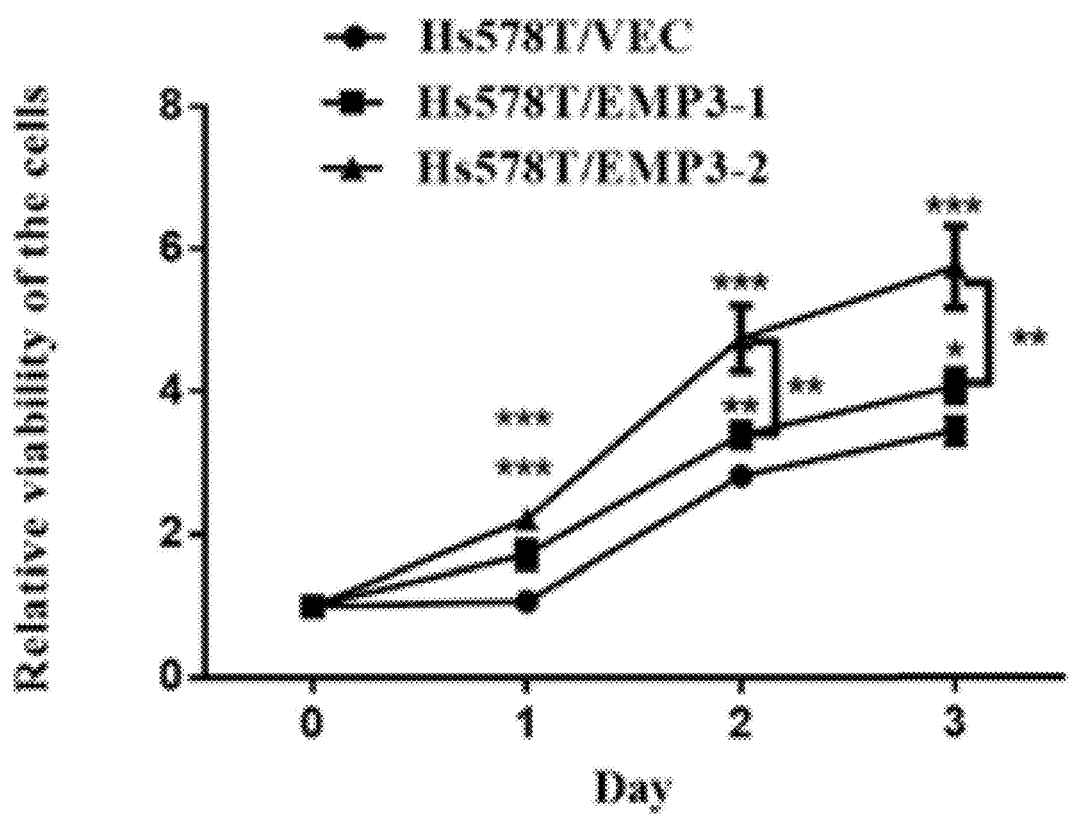
FIG. 2B is line graph to illustrate in vitro proliferation ability of Hs578T cells overexpressing EMP3.

Please refer to FIG. 2A to 2D illustrating biologic effects of EMP3 on human breast cancer in vitro including cell growth, cell migration and cell invasion. As shown in FIG. 2A, both HS578T-EMP3-1 and HS578T-EMP3-2 stable clones showed a higher level of EMP3 protein expression compared to control cells (HS578T-Vec). As shown in FIG. 2B, overexpression of EMP3 dose-dependently promoted cell proliferation in vitro than control cells (*$P<0.05$; $P<0.01$; *$P<0.001$; two-way ANOVA).

Figure 2C:
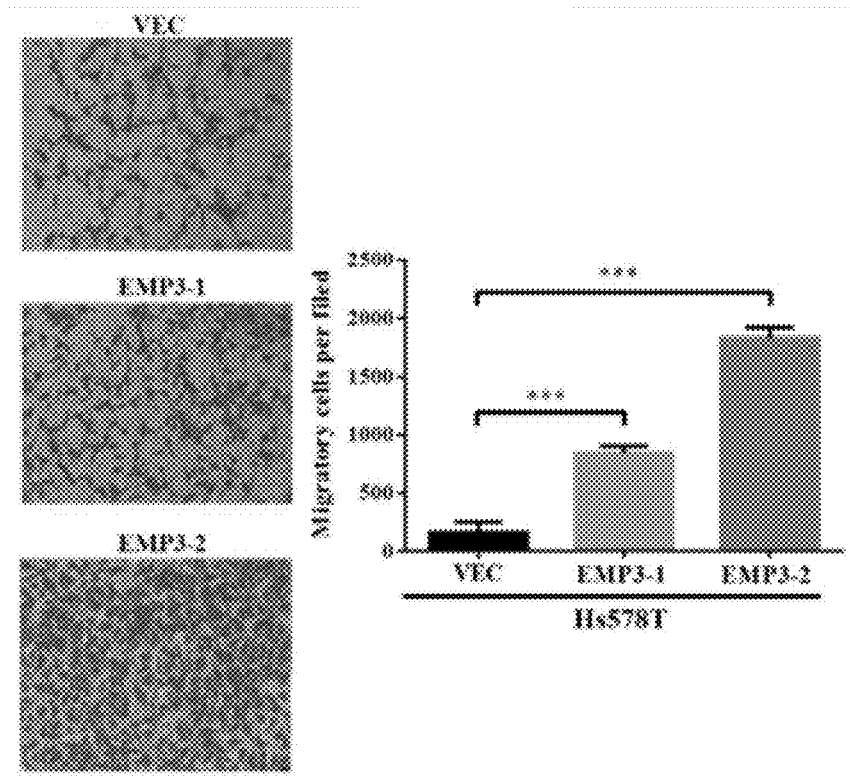
FIG. 2C illustrates effects of EMP3 overexpression on in vitro cell migration ability of Hs578T cells.
Figure 2D:
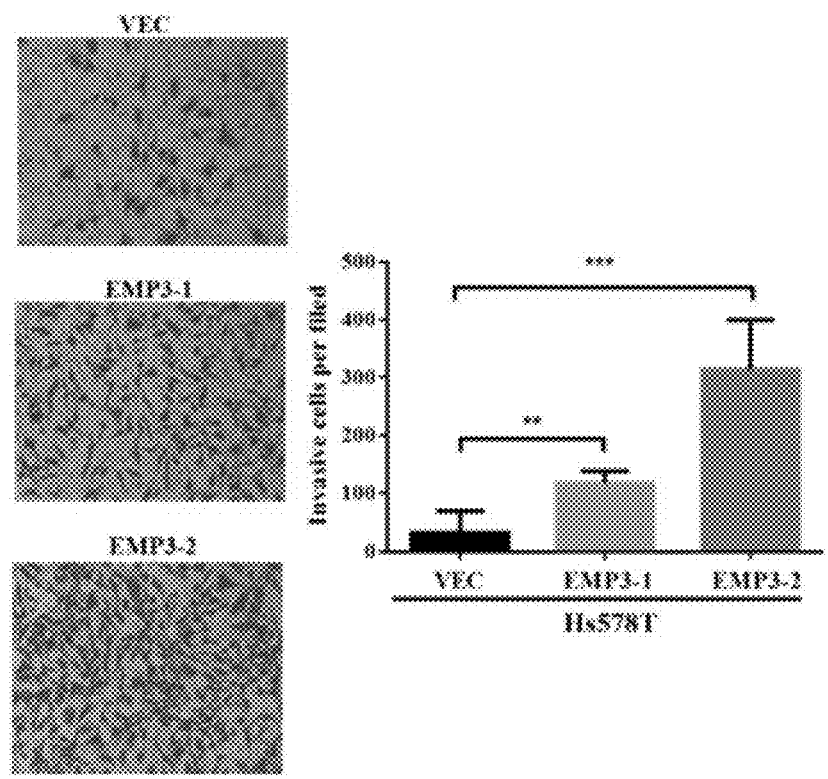
FIG. 2D illustrates effects of EMP3 overexpression on in vitro invasion ability of Hs578T cells.

In addition, as shown in FIG. 2C to 2D, HS578T-EMP3 stable cells exhibited an enhanced migration in Transwell assay (*$P<0.05$; two-tailed t-test) and invasion in Matrigel assay (**$P<0.01$; *$P<0.05$, two-tailed t-test) than vector control. The impact of EMP3 on cell migration was also examined using wound healing assay. The closure of wounding by Hs578T-EMP3 stable cells was faster than that of Hs578T-Vec cells ($p<0.01$, respectively).

Figure 3A:
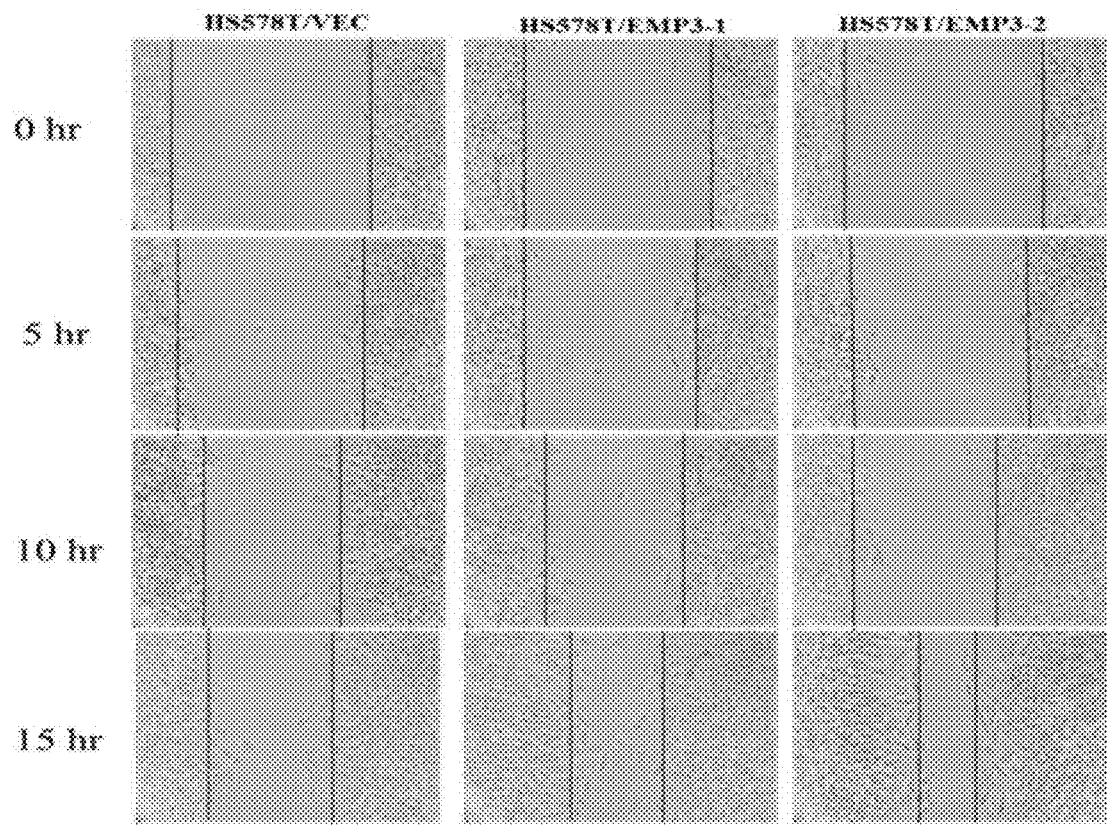
FIG. 3A illustrates wound healing assays for assessing effects of EMP3 overexpression on Hs578T cells.
Figure 3B:
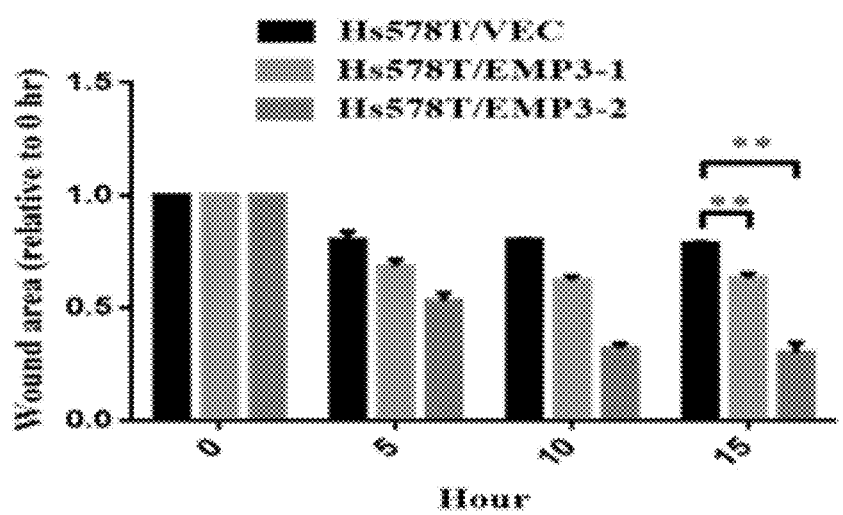
FIG. 3B is a bar chart illustrating analytic results of wound healing assays.

Furthermore, in order to test EMP3's effect on cell migration, wound-healing experiments were therefore established for testing thereof. Please refer to FIG. 3A to 3B, effects of EMP3 on breast cancer cell migration were evaluated by wound-healing experiments. As shown in FIG. 3A, Hs578T cells were seeded and cultured at cell density of $2 \times 10^5$ cells per insert, and wounding was created by culture insert. In order to evaluate cell migration ability, area between wounding edge was estimated at 5, 10 and 15 hours after EMP3 transduction, respectively. As shown in FIG. 3B, the images were captured and area between wounding edges were measured using Image J software to evaluate the healing condition. The graph represents the average values and standard errors of four independent experiments. Overexpression of EMP3 stimulated cell migration in vitro than control (p=0.00592 and 0.0016, respectively). Compared with control cells, Hs578T-EMP3 closed the wound faster. (p<0.01)

In other aspects, positive effects of EMP3 on cell growth, migration and invasion in vitro was also observed in MDA-MB-231 cells (data not shown).

Example 2: Cross-Talk of EMP3 with HER Family in Human Breast Cancer Cells

To verify the functional cross-talk of EMP3 with HER2 in vitro, stable clones were examined for expression of HER2, other HER subfamily members and hormone receptors. It is shown that EMP3 overexpression significantly activates the expression of EGFR, HER2 and HER3, but down-regulates the HER4.

Figure 4:
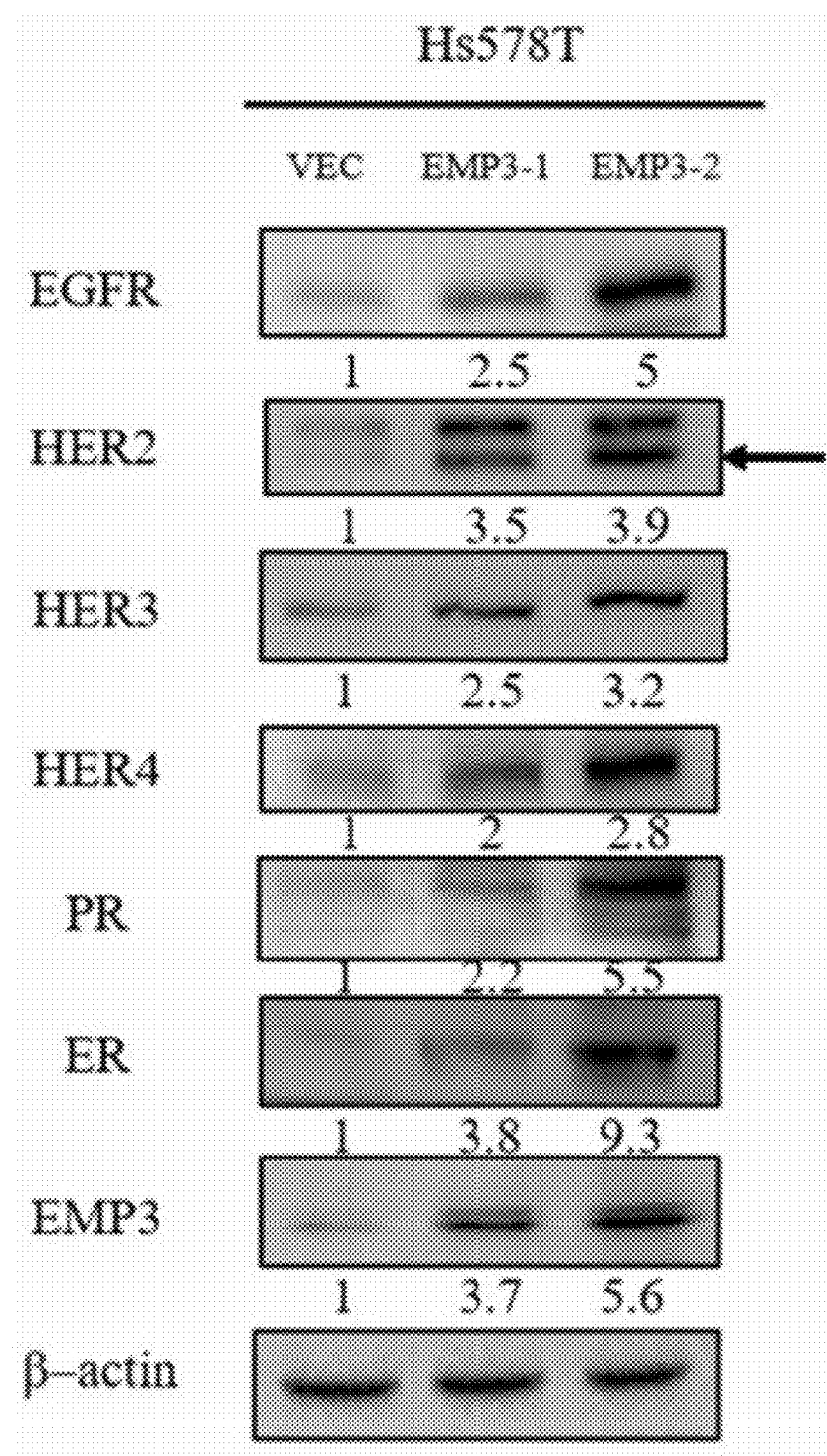
FIG. 4 is a western blot to illustrate crosstalk of EMP3 with HER family and hormone receptors in human breast cancer cells in vitro.

EMP3 overexpression stable cells were established on Hs578T cells. Cell extracts were fractionated by 6% to 12% SDS-PAGE gradient gel under reducing conditions and probed with appropriate antibodies. As shown in FIG. 4, overexpression of EMP3 dose-dependently up-regulated the expression of EGFR, HER2, HER3, HER4 and hormone receptors. The results had been validated by triplicate experiments. A mildly increased expression of PR was demonstrated, but no apparent effect was observed for ER. A comparable effect was also observed in MDA-MB231 cells. Accordingly, EMP3 expression could transactivate HER family expression in human BC in vitro.

Example 3: Effects of EMP3 on Breast Cancer Cells' Biological Functions

Figure 5A:
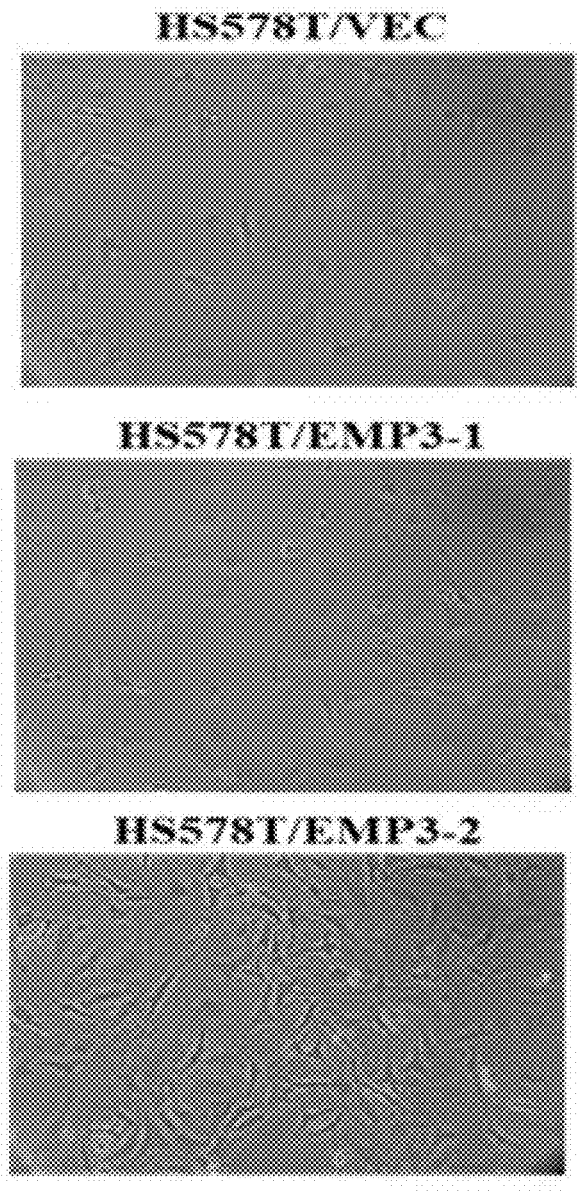
FIG. 5A is a cell image demonstrating cytomorphology of EMP3-overexpressing Hs578T cells with overexpression of EMP3.
Figure 5B:
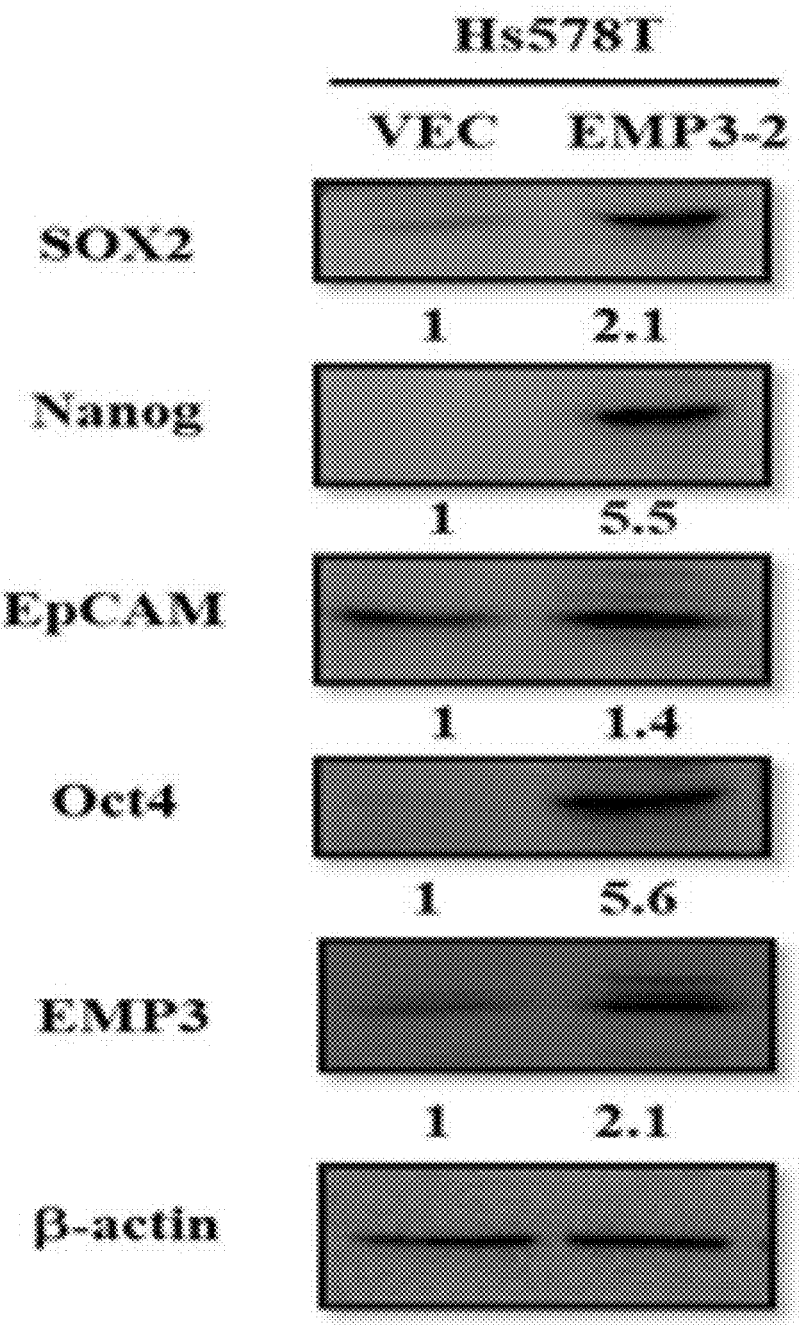
FIGS. 5B and 5C are western blots for evaluating protein expression levels of EMP3, stem cell markers and epithelial-mesenchymal cell markers in EMP3-overexpressing Hs578T cells.
Figure 5C:
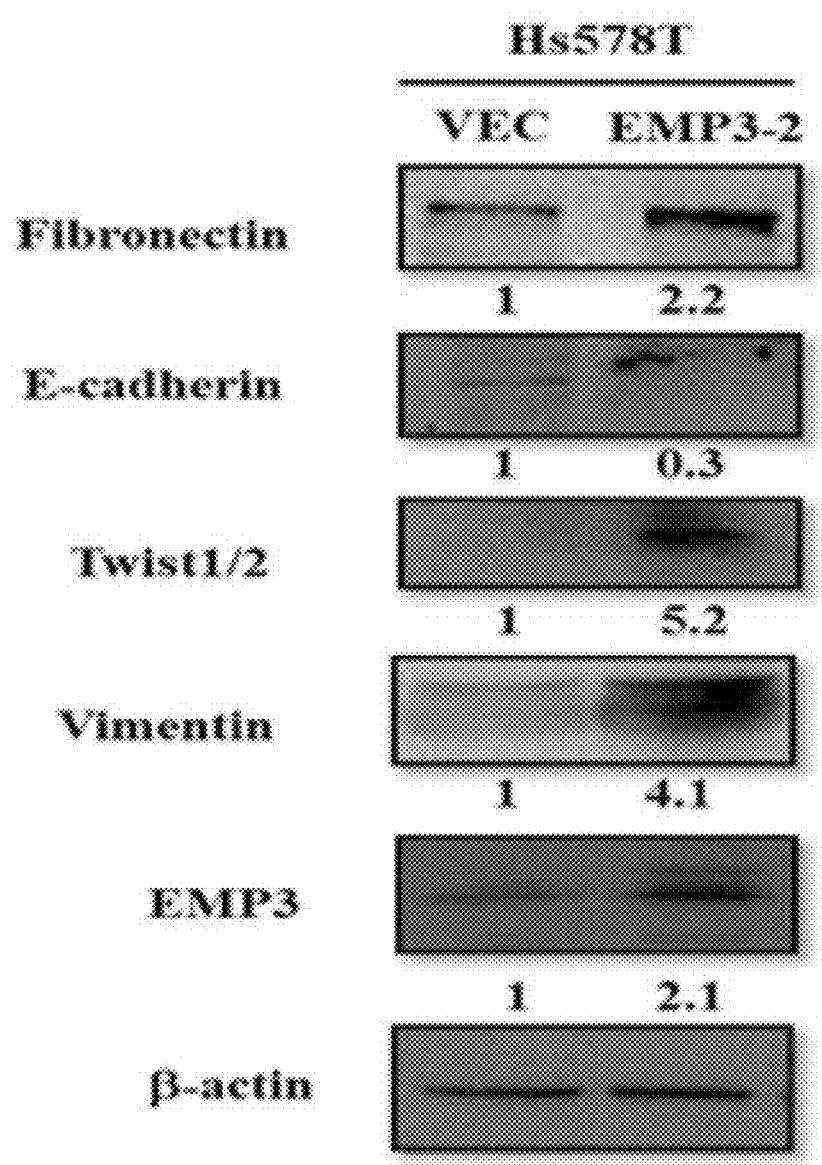

Please refer to FIGS. 5A to 5C illustrating effects of EMP3 on EMT and stemness of breast cancer cells. As shown in FIG. 5A, Hs578T-EMP3 stable cells, especially Hs578T-EMP3-2 cells, exhibited fibroblastoid morphology and long slender processes when compared with control cells (Hs578T-Vec). Thus, the potential effects of EMP3 on EMT of BC cells were further examined. As shown in FIGS. 5B and 5C, EMP3 overexpression up-regulated fibronectin, Twist1/2, and vimentin, but suppressed E-cadherin expression. Moreover, EMP3 was shown to activate the expression of stemness target genes such as SOX2, Nanog, EpCAM and Oct4.

Example 4: Signaling Pathways Modulated by EMP3 in Human Breast Cancer

A cross-talk between EMP2 and integrins αV and β3 in the regulation of urothelial cell adhesion and migration in vitro has been previously reported. Thus, the effects were investigated in BC at the cellular level.

In example 4, cell extracts from Hs578T-EMP3 were fractionated by 6% to 12% SDS-PAGE gradient gel under reducing conditions and probed with antibody to EGFR, EMP3, FAK, Src, phospho-Src, ROCK1, ROCK2, β-actinin, phospho-MBS, JAK2, phospho-JAK2, STAT3, RAS, RAF-1, ERK1/2, PI3K, AKT and mTOR, respectively. The β-actin was used as a loading control. Band density was quantified and expressed as ratios related to vector cells.

Figure 6:
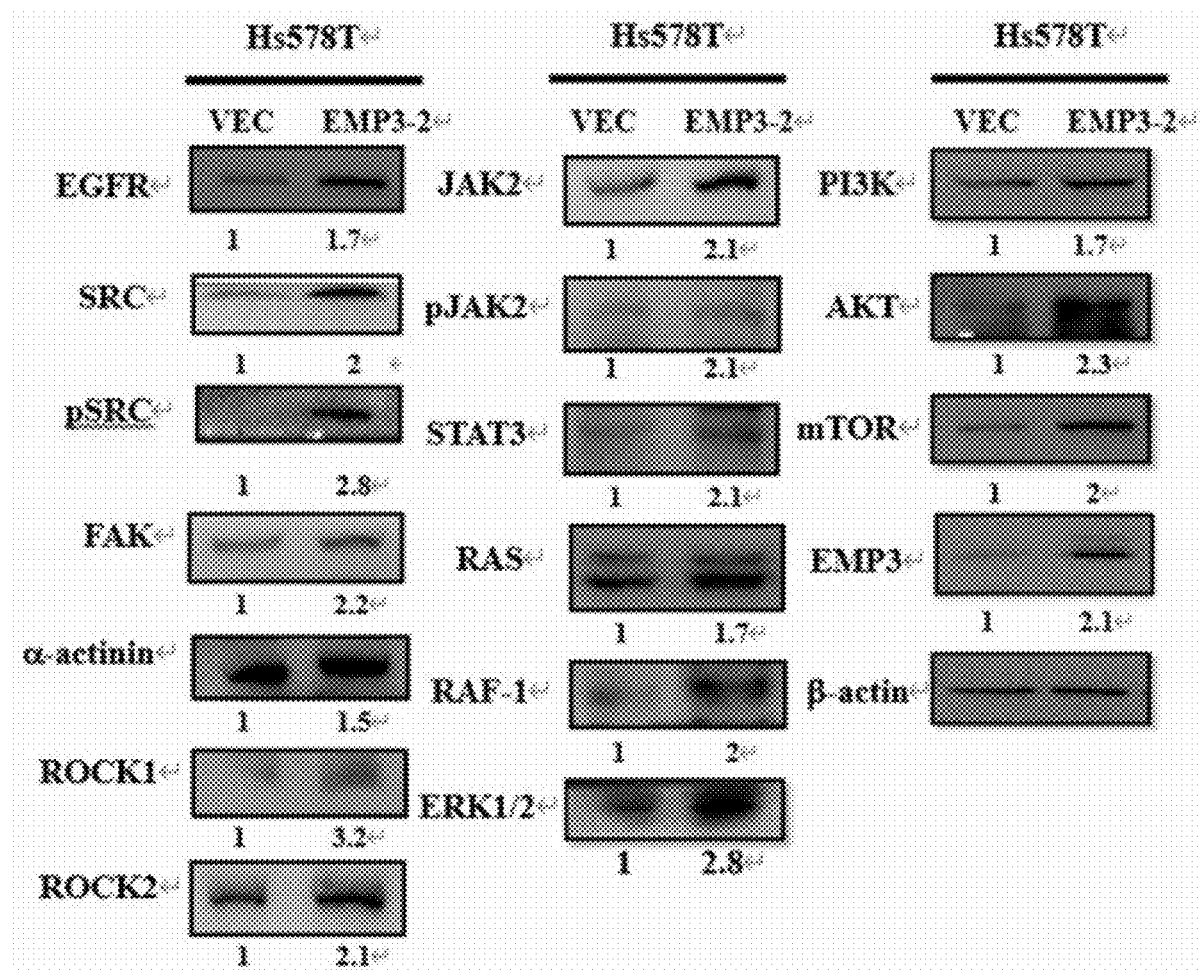
FIG. 6 is a western blot to illustrate effects of EMP3 on FAK/c-Src signal pathway in vitro.

As shown in FIG. 6, immunoblotting showed that EMP3 up-regulated the expression of FAK-Src-RhoA, Src-JAK2-STAT3, Src-Ras/Raf-1, and ERK1/2. Together, EMP3 over-expression activated the FAK/c-Src signaling pathway of human breast cancer cells in vitro.

Example 5: Biological Effects of EMP3 Targeting on Human Breast Cells In Vitro As shown above, EMP3 potentially functions as an onco-gene for human BC, and could transactivate the HER receptor expression and multiple signaling pathways. To translate into BC patient care, the potential of EMP3 as a therapeutic target was further evaluated and verified in example 5.

Figure 7A:
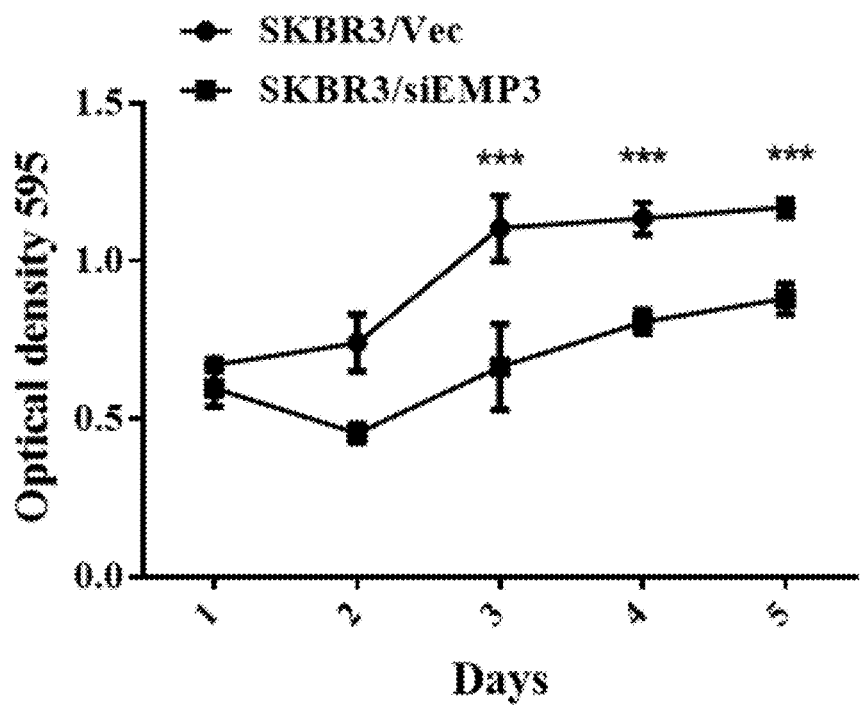
FIG. 7A is a line graph to demonstrate cell proliferation rate measured by MTT assays.
Figure 7B:
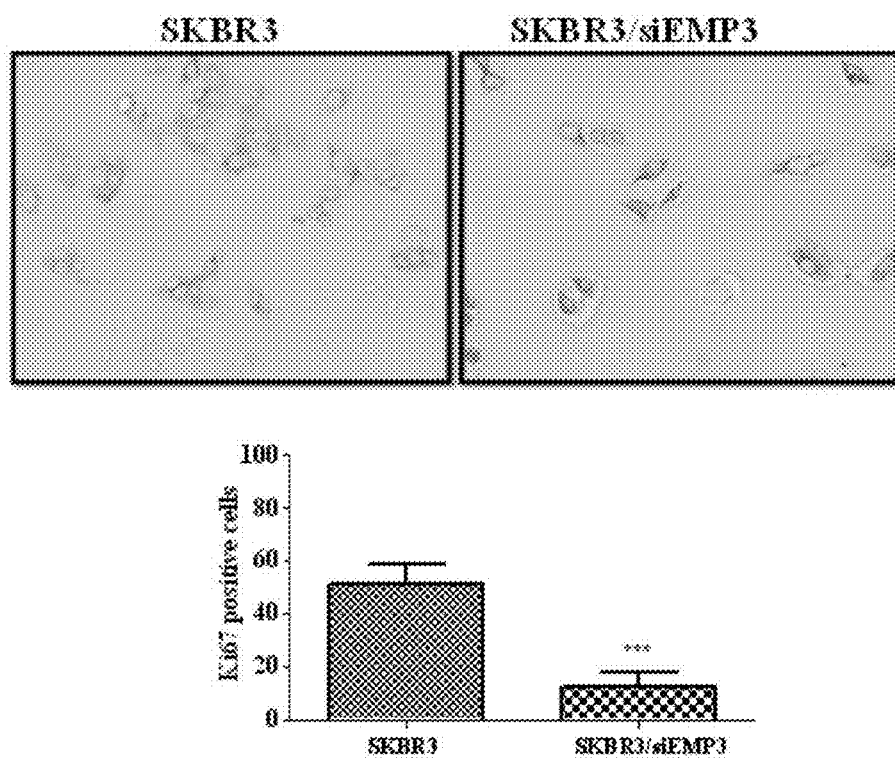
FIG. 7B illustrates the effect of EMP3 on cell proliferation estimated by Ki-67 index after transient transfection.

In example 5, the HER3-overexpressing SKBR3 (ATCC HTB-30) cell line was chosen to test the instant applicant's hypothesis. FIGS. 7A to 7B illustrate EMP3's effects on breast cancer cell proliferation in vitro. Through MTT assays, knock-down of EMP3 significantly suppressed the growth of SKBR3 cells in vitro (P<0.0001, two-way ANOVA) and Ki-67 index measurement (P<0.005, paired t-test) compared with SKBR3/Vec control cells.

Figure 8:
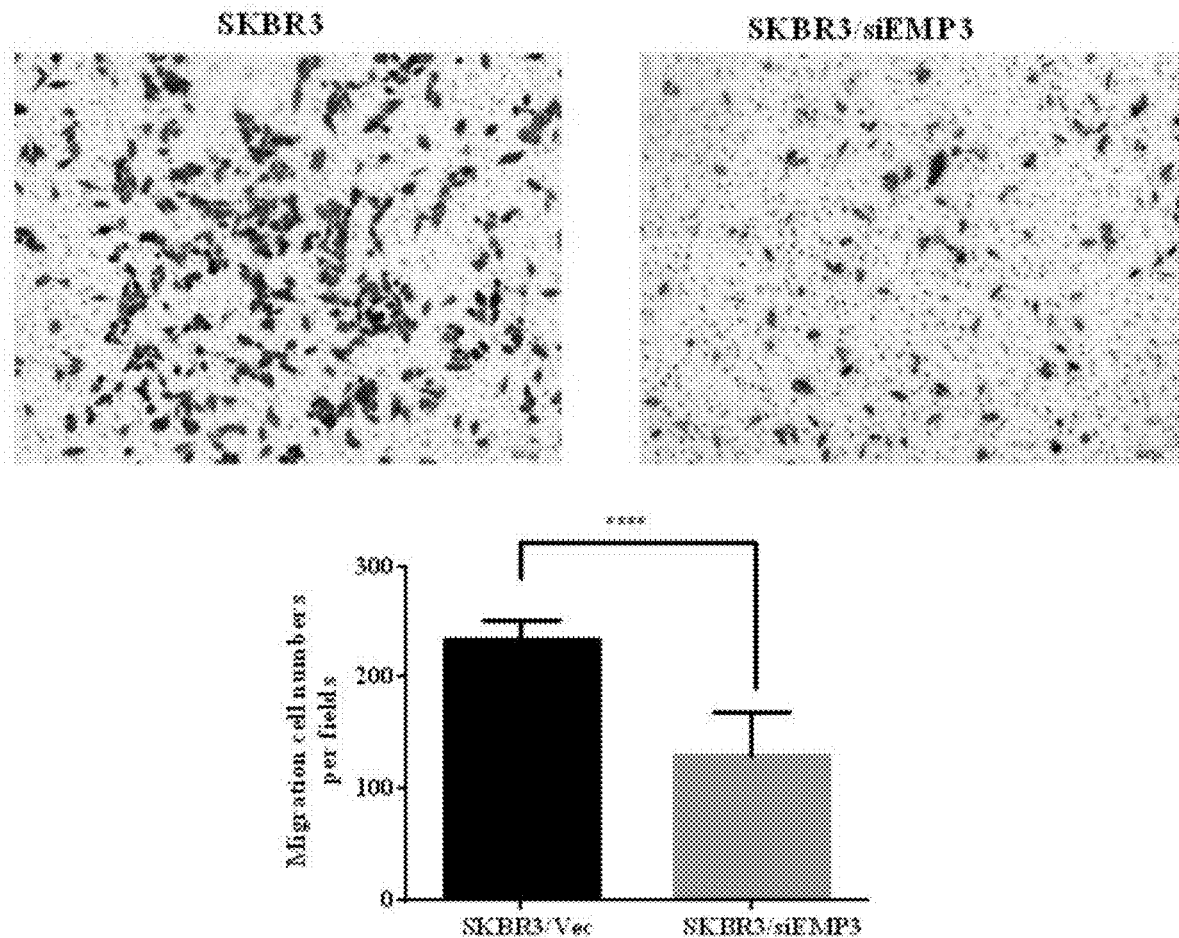
FIG. 8 illustrates effect of EMP3 on cell migration in vitro by performing Boyden chamber assay to measure cell migration.
Figure 9:
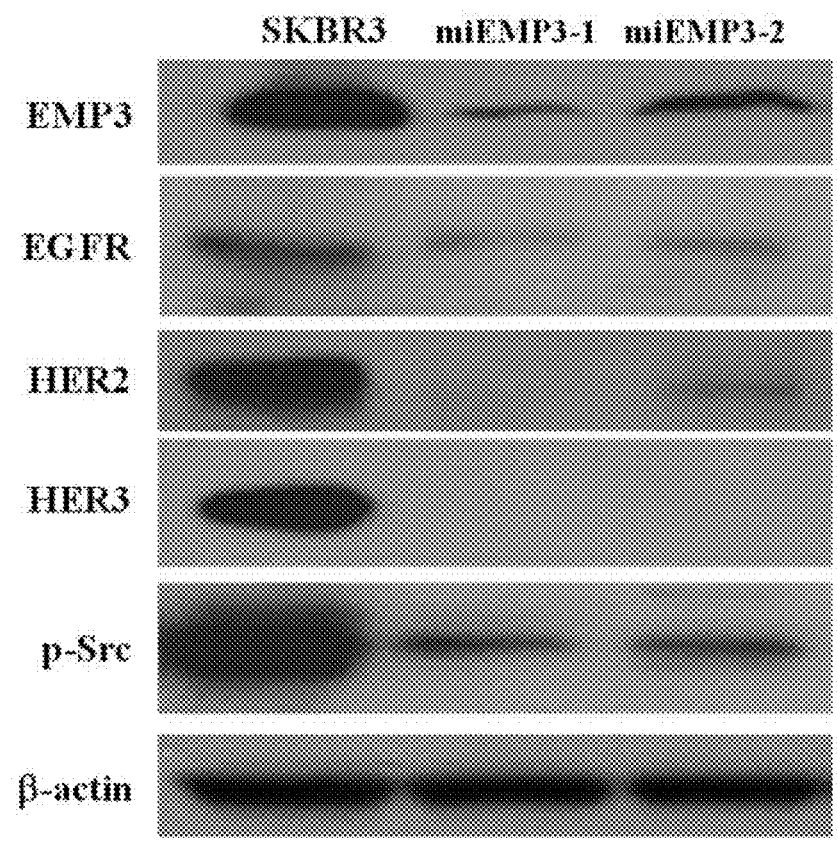
FIG. 9 is a western blot for illustrating modulation of EGFR, HER2, HER3 and phosphor-Src by EMP3 in human breast cancer cells in vitro.

Furthermore, FIG. 8 illustrates the influences of EMP3 on suppressing cell migration. The inhibitory effect on cell migration after knocking down of EMP3 was significant when compared with control cells. (P<0.005, paired t-test). In addition, as shown in FIG. 9, expression of EGFR, HER2, HER3 and p-Src was all down-regulated in SKBR3 EMP3 knock-down stable clones.

Example 6: Xenograft Model of EMP3 Targeting for Human Breast Cells

Figure 10:
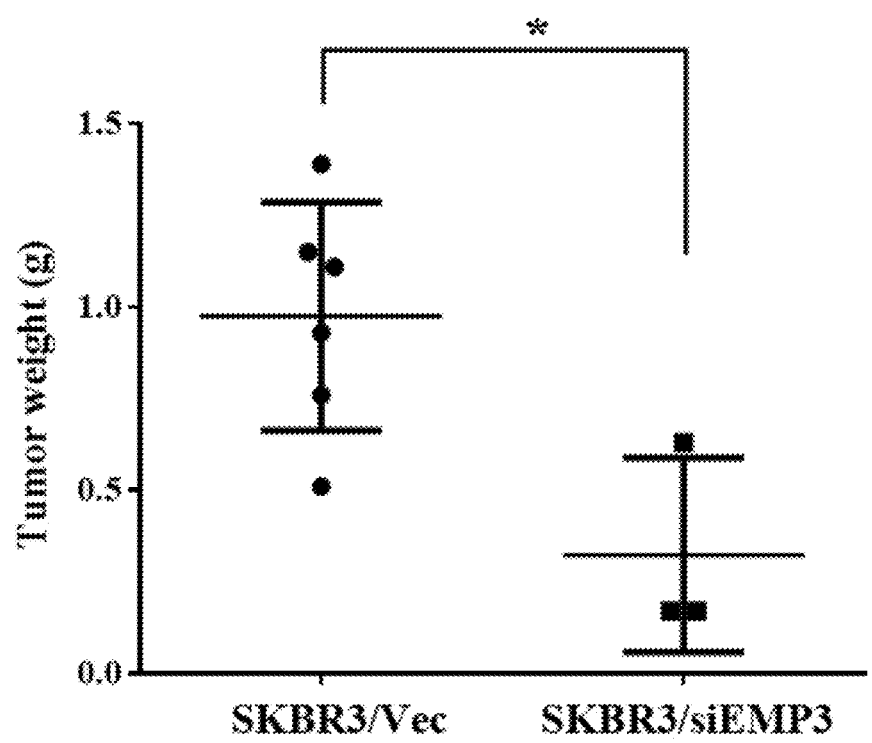
FIG. 10 demonstrates effects of EMP3 on tumorigenicity of breast cancer cells in vivo.

To verify the clinical implication of EMP3 targeting for BC, SCID animal experiment was carried out. As shown in FIG. 10, the SKBR3/siEMP3 stable clones developed smaller tumors in the subcutis of mice than that of vector controls (P<0.001). To be specific, appropriate stable SKBR3/V or SKBR3/siEMP3 cells ($1\times10^7$) were injected to SCID mice by subcutaneous route for assessing the tumorigenic potential of EMP3 with or without HER2. The tumor nodules were measured regularly for 23 days. As shown in FIG. 10, tumor weight of SKBR3/siEMP3 (EMP3 knock-down) cells was significantly lower than that of SKBR3/Vec cells (**P<0.001).

Figure 11A:
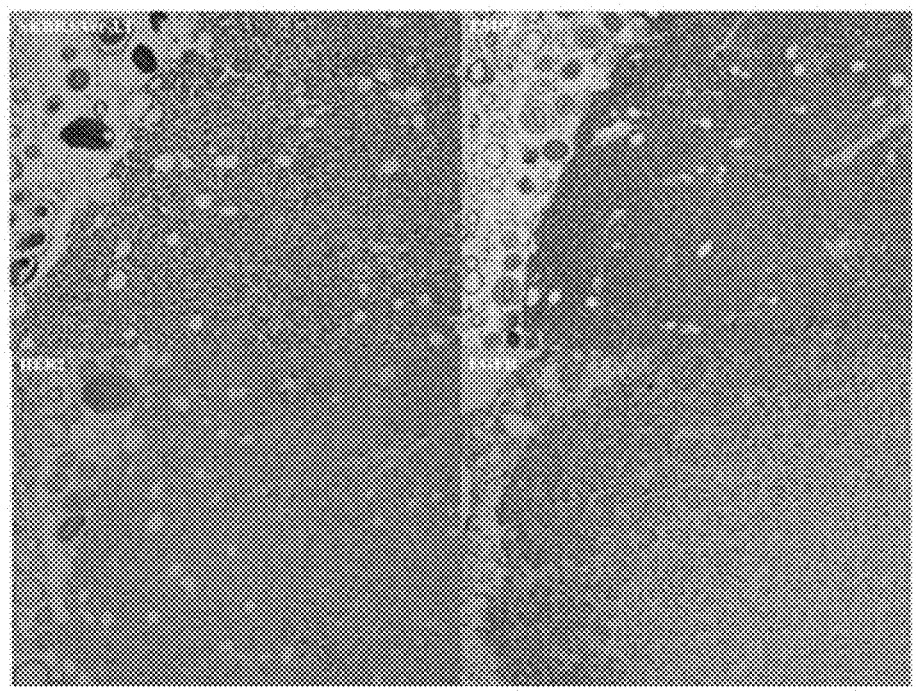
FIGS. 11A to 11B are immunohistochemical staining for evaluating protein expression levels of cell surface biomarkers in xenograft tumors in SCID mice.
Figure 11B:
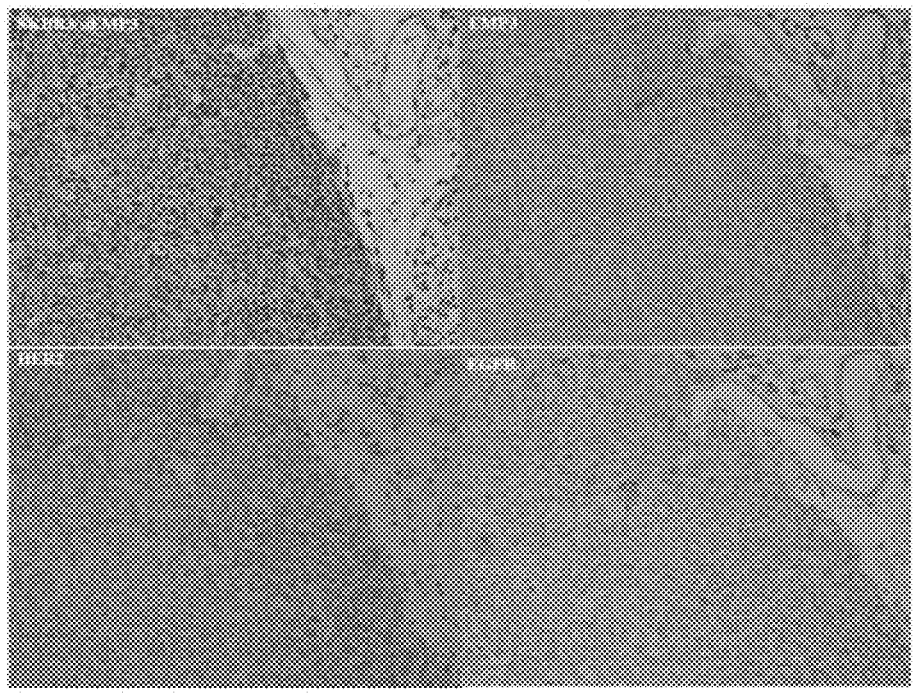

In other words, tumor size on mice back after subcutaneous injection of SKBR3/siEMP3 was smaller than that of control cells. On the other hand, biomarker expression of EMP3, EGFP and HER2 in vivo was examined by IHC. As shown in FIG. 11A, a strong membranous expression of EMP3, EGFR and HER2 was demonstrated in the tumors of SKBR3/Vec cells, whereas expression of these biomarkers was all inhibited in tumors of SKBR3/siEMP3 stable cells as shown in FIG. 11B. All of tumor tissue were comprehensively evaluated and scored for staining results. Tumors showing EGFR, HER2 and HER3 immunostaining in less than 5% of tumor cells or a lack of any immunoreactivity were classified as negative expression. Those with a staining reaction greater than 5% were defined as positive expression. For EMP3, a two-scale scoring system was used based on the proportion of tumor cells stained. The "positive expression" indicates that greater than 20% of tumor cells were stained, while "negative expression" indicates that less than 20% were stained for EMP3 antibody.

Example 7: Chemoprevention Model for EMP3-Related BC

Metformin, a first-line oral antidiabetic drug for adult and pediatric type 2 diabetes, has long been known to promote its lipid-lowering and insulin sensitivity-improving actions in liver and pancreatic cells. Experiments in vitro and in vivo also demonstrated the potential of Metformin to block precancerous lesions progression to invasive tumors. Thus, Metformin is greatly potential to be an anti-tumor agent for preventing the progression of breast tumorigenesis.

Figure 12A:
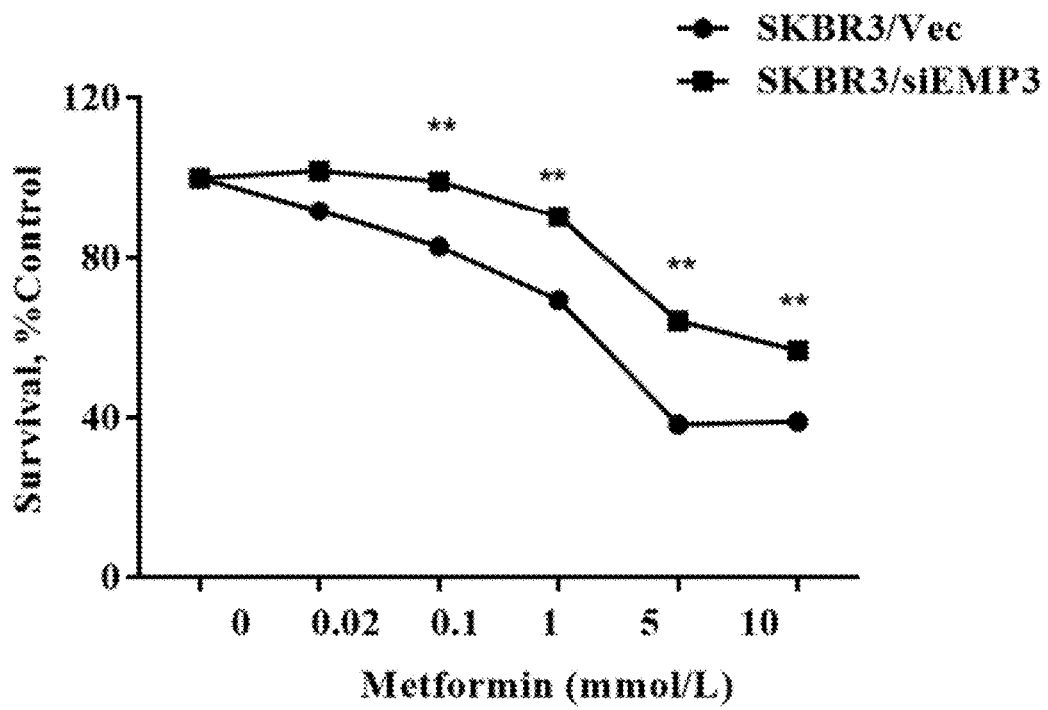
FIG. 12A is a line graph for measuring $IC_{50}$ of SKBR3/Vec cells and SKBR3/siEMP3 cells upon administration of Metformin.
Figure 12B:
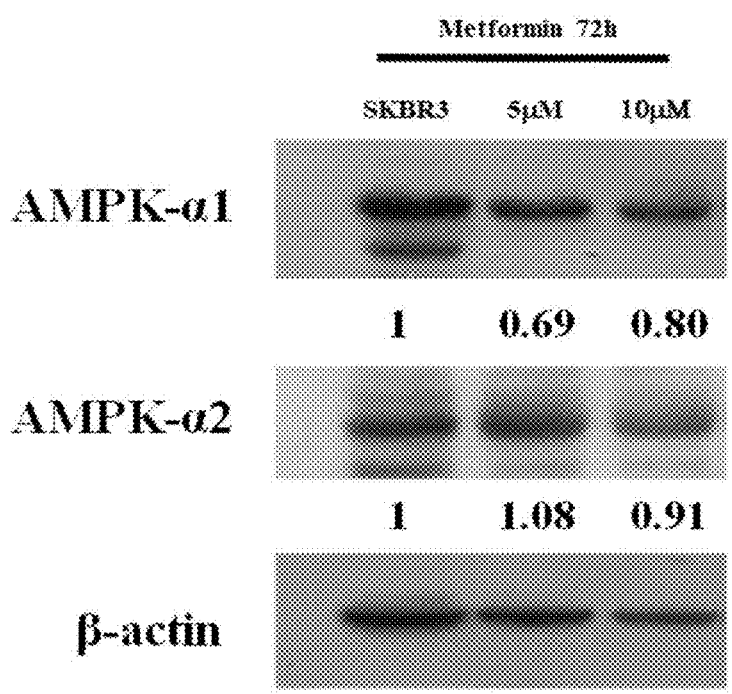
FIG. 12B is a western blot illustrating effect of Metformin on AMPK signaling pathway in SKBR3 cells.

However, experiments in example 7 demonstrated that the SKBR3/Vec cells are more sensitive to Metformin treatment compared with SKBR3/siEMP3 cells in vitro. The result suggests that Metformin may have off-target effect on EMP3-related events in human breast cancer. Please refer to FIGS. 12A to 12B. The potential impact of EMP3 on sensitivity to Metformin in SKBR3 cells in vitro was illustrated therein. As shown in FIG. 12A, SKBR3/Vec and SKBR3/siEMP3 cancer cells were treated with Metformin at various concentrations, and the $IC_{50}$ values of Metformin were measured for SKBR3/Vec and SKBR3/siEMP3 cancer cells at 72 hours post treatment, respectively. FIG. 12A showed that SKBR3/siEMP3 cells had higher $IC_{50}$ values for Metformin than vector control in vitro. That means knocking down of EMP3 raises survival rate of breast cancer cells upon treatment of Metformin, which may imply a desensitizing effect of EMP3 on breast cancer cells in upon Metformin treatment. Furthermore, as shown in FIG. 12B, Metformin down-regulated AMPK-α1 and AMPK-α2 in SKBR3 cells. As well-known in the field of endeavor, interference of cross-talk between AMPK and Wnt/β-catenin signaling pathways may decelerate cell growth of breast cancer cells. In example 7, the intervention level of Metformin to AMPK in SKBR3/Vec and SKBR3/siEMP3 cancer cells was verified. Breast cancer cell line with knockdown of EMP3 demonstrated higher survival rate than control cells, and also less sensitive to Metformin treatment at AMPK signaling pathway level.

The targeted therapy composition provided in present invention is characterized by its targeting effect on breast cancer cells. The composition suppresses EMP3 and interferes breast cancer cell biological functions, such as cell proliferation, migration and invasion. Thus the composition can significantly slow down breast cancer cell proliferation and tumor metastasis in vivo.

The targeted therapy composition provided in present invention can be administrated with Metformin so as to reduce proliferation rate of breast cancer cells by EMP3 targeting effect of the composition. The composition can be administrated with Metformin sequentially or separately to lower breast cancer cell survival rate as well as tumor growth and metastasis.

The targeting therapy composition provided in present invention offers breast cancer patients more options. In addition to lowering breast cancer cell proliferation and metastasis, the composition can be administrated with a first-line anti-diabetic drug, Metformin, sequentially or separately, so as to control diabetes and to treat breast cancer at mean time.

---

What is claimed is:

1. A method for suppressing breast cancer cell proliferation, migration or invasion, comprising administrating a targeted therapy composition comprising an effective dosage of EMP3-targeting inhibitor to a subject in need thereof;
wherein the EMP3-targeting inhibitor comprises RNA interference comprising a small interfering RNA, short hairpin RNA, microRNA or a combination thereof, and the RNA interference hybridizes with EMP3 coding DNA or mRNA by complementary base pairing;
wherein the RNA interference comprises a complementary sequence including SEQ NO: 1 or SEQ NO: 2.

2. The method as claimed in claim 1, comprising sequentially or separately administrating the targeted therapy composition and Metformin to the subject in need, wherein the targeted therapy composition is administrated to the subject in need when Metformin is completely excreted, or the targeted therapy composition is administrated to the subject in need at 24 hours post Metformin administration.

3. The method as claimed in claim 2, wherein the subject in need is human (*Homo sapiens*) having diabetes.

4. The method as claimed in claim 1, wherein the breast cancer cell is selected from a group consisting of hormone receptor (HR) positive breast cancer cell, human epidermal growth factor receptor 2 (HER2) positive breast cancer cell and triple negative breast cancer cell.

5. The method as claimed in claim 1, wherein the complementary sequence hybridizes to a nucleotide sequence of 61st to 180th or 241st to 360th base pairs of the mRNA by complementary base pairing, wherein the mRNA consists of SEQ NO: 5.

6. A method for suppressing breast cancer cell proliferation, migration or invasion, comprising administrating a targeted therapy composition comprising an effective dosage of EMP3-targeting inhibitor to a subject in need thereof;
wherein the EMP3-targeting inhibitor comprises a plasmid DNA fragment carried by a vector comprising a promoter upstream the plasmid DNA fragment so as to amplify productions of a RNA interference, and the RNA interference hybridizes with EMP3 coding DNA or mRNA by complementary base pairing;
wherein the plasmid DNA fragment comprises SEQ NO: 3 or SEQ NO: 4.

7. The method as claimed in claim 5, wherein the RNA interference comprises a complementary sequence, and the complementary sequence hybridizes to a nucleotide sequence of 61st to 180th or 241st to 360th base pairs of the mRNA by complementary base pairing, wherein the mRNA consists of SEQ NO: 5.

8. The method as claimed in claim 6, wherein the RNA interference comprises a small interfering RNA, short hairpin RNA, microRNA or a combination thereof, and wherein the complementary sequence comprises SEQ NO: 1 or SEQ NO: 2.

9. The method as claimed in claim 6, comprising sequentially or separately administrating the targeted therapy composition and Metformin to the subject in need, wherein the targeted therapy composition is administrated to the subject in need when Metformin is completely excreted, or the targeted therapy composition is administrated to the subject in need at 24 hours post Metformin administration.

10. The method as claimed in claim 6, wherein the subject in need is human (*Homo sapiens*) having diabetes.

11. The method as claimed in claim 10, wherein the breast cancer cell is selected from a group consisting of hormone receptor (HR) positive breast cancer cell, human epidermal growth factor receptor 2 (HER2) positive breast cancer cell and triple negative breast cancer cell.

* * * * *

SEQUENCE LISTING

```
Sequence total quantity: 5
SEQ ID NO: 1              moltype = RNA  length = 21
FEATURE                   Location/Qualifiers
source                    1..21
                          mol_type = other RNA
                          organism = synthetic construct
SEQUENCE: 1
ccttcacatc ctcattctta t                                             21

SEQ ID NO: 2              moltype = RNA  length = 21
FEATURE                   Location/Qualifiers
source                    1..21
                          mol_type = other RNA
                          organism = synthetic construct
SEQUENCE: 2
cattctctgc tgtctctcct t                                             21

SEQ ID NO: 3              moltype = DNA  length = 21
FEATURE                   Location/Qualifiers
source                    1..21
                          mol_type = other DNA
                          organism = synthetic construct
SEQUENCE: 3
ccttcacatc ctcattctta t                                             21

SEQ ID NO: 4              moltype = DNA  length = 21
FEATURE                   Location/Qualifiers
source                    1..21
                          mol_type = other DNA
                          organism = synthetic construct
SEQUENCE: 4
cattctctgc tgtctctcct t                                             21

SEQ ID NO: 5              moltype = RNA  length = 649
FEATURE                   Location/Qualifiers
source                    1..649
                          mol_type = mRNA
                          organism = Homo sapiens
SEQUENCE: 5
ggaggcccga gcgagggaca agactccgac tccagtctg  acttttttcg cggctctcgg   60
cttccactgc agccatgtca ctcctcttgc tggtggtctc agcccttcac atcctcattc  120
ttatactgct tttcgtggcc actttggaca agtcctggtg gactctccct gggaaagagt  180
ccctgaatct ctggtacgac tgcacgtgga acaacgacac caaaacatgg gcctgcagta  240
atgtcagcga gaatggctgg ctgaaggcgg tgcaggtcct catggtgctc tccctcattc  300
```

```
tctgctgtct ctccttcatc ctgttcatgt tccagctcta caccatgcga cgaggaggtc    360
tcttctatgc caccggcctc tgccagcttt gcaccagcgt ggcggtgttt actggcgcct    420
tgatctatgc cattcacgcc gaggagatcc tggagaagca cccgcgaggg ggcagcttcg    480
gatactgctt cgccctggcc tgggtggcct tccccctcgc cctggtcagc ggcatcatct    540
acatccacct acggaagcgg gagtgagcgc cccgcctcgc tcggctgccc ccgcccttc     600
ccggccccc  tcgccgcgcg tcctccaaaa aataaaacct taaccgcgg                649
```